United States Patent
Bhandakar et al.

(10) Patent No.: US 7,752,887 B2
(45) Date of Patent: Jul. 13, 2010

(54) DETECTION OF IMPURITIES IN GAS STREAMS

(75) Inventors: Maruti Bhandakar, E. Weymouth, MA (US); Joseph Peters, Quincy, MA (US)

(73) Assignee: Stone & Webster, Inc., Houston, TX (US)

( * ) Notice: Subject to any disclaimer, the term of this patent is extended or adjusted under 35 U.S.C. 154(b) by 270 days.

(21) Appl. No.: 12/017,819

(22) Filed: Jan. 22, 2008

(65) Prior Publication Data

US 2009/0183553 A1    Jul. 23, 2009

(51) Int. Cl.
G01N 21/06    (2006.01)
G01N 27/00    (2006.01)

(52) U.S. Cl. .................. 73/31.03; 356/409; 436/139; 422/86; 422/88

(58) Field of Classification Search ............. 73/31.03; 356/409; 422/86, 88; 436/141, 142
See application file for complete search history.

(56) References Cited

U.S. PATENT DOCUMENTS

| | | | | |
|---|---|---|---|---|
| 2,429,694 A | * | 10/1947 | King | .................. 436/39 |
| 2,487,077 A | * | 11/1949 | Shepherd | .................. 436/134 |
| 3,223,487 A | * | 12/1965 | Karl Grosskopf | .................. 422/86 |
| 3,388,975 A | * | 6/1968 | Wallace | .................. 422/59 |
| 3,661,009 A | * | 5/1972 | Leonard et al. | .................. 73/31.03 |
| 5,583,282 A | * | 12/1996 | Tom | .................. 73/31.03 |

OTHER PUBLICATIONS

G. Bellussi, G. Pazzuconi, C. Perego, G. Girotti, and G. Terzoni, "Liquid-Phase Alkylation of Benzene with Light Olefins Catalyzed by β Zeolites." Journal of Catalysts 157, pp. 227-234. (1995).*

* cited by examiner

*Primary Examiner*—Lisa M Caputo
*Assistant Examiner*—Punam Roy

(57) ABSTRACT

A method of measuring the level of an impurity in a gas comprises providing a gas detection tube having a internal volume containing a reagent which can react with said impurity to produce a compound capable of producing a color change in said tube such that the extent of the color change is proportional to the concentration of the impurity in said gas. A volume of the gas at least $1 \times 10^3$ times the test volume of the gas detection tube is passed through the tube and the extent of the color change of the detector element is measured.

19 Claims, 1 Drawing Sheet

_US 7,752,887 B2_

DETECTION OF IMPURITIES IN GAS STREAMS

FIELD

This invention relates to a method of detecting and measuring low levels of impurities in gas streams and in particular low levels (less than 0.5 ppm) of impurities in light hydrocarbon ($C_1$ to $C_4$) streams.

BACKGROUND

In many chemical processes, it is important to be able to detect even very low levels of impurities in the feed streams to the process so that, if necessary, appropriate steps can be taken to remove, and/or mitigate the deleterious effect of, these impurities. For example, it is well known that zeolite catalysts are highly sensitive to basic impurities, such as nitrogen compounds and arsine, particularly when used in low temperature, liquid-phase processes, such as the liquid-phase alkylation of benzene with $C_2$ to $C_4$ olefins.

Various methods are currently available for detecting impurities in feed streams, but in general these methods have limited utility with low concentrations of impurity and/or have limited effectiveness with certain important combinations of feed stream and impurity type. For example, chemiluminescence detection is a standard method of detecting a wide range of nitrogen impurities in liquid hydrocarbons, but its detection limit is normally of the order of 0.3 ppm of nitrogen. Moreover, chemiluminescence is not a reliable method of detecting nitrogen impurities in light olefinic feedstreams due to their relatively high heat of combustion which may cause interference in the detection system. Similarly, although ion selective electrodes can be used to detect low levels of specific nitrogen impurities, such as ammonia or hydrogen cyanide, in olefinic feed streams, the method does not work well with light alkyl amine impurities. In addition, both chemiluminescence and ion selective electrodes are part of complex procedures requiring expensive laboratory instrumentation and facilities, and so cannot readily be employed in situ at chemical process sites.

In fact, there is currently no generally accepted standard method available for the detection of nitrogen impurities in light hydrocarbon gases below 0.1 ppm. There is therefore a need for an improved method of detecting and measuring the level of impurities, such as ammonia, alkylamines, nitriles, cyanides and arsine, in gas streams, such as light hydrocarbon ($C_1$ to $C_4$) streams, especially when the impurities are present at very low levels, for example less than 0.5 ppm and even less than 0.05 ppm.

In the field of air quality monitoring, it is known to test for a given component by drawing a small specified amount of air, typically 100 to 400 cc, through a gas detection tube with a hand-operated pump. The tube contains a reagent which reacts selectively with the component to be measured to produce a compound which either directly or indirectly produces a color change. By measuring the extent of the color change, the amount of the component in the air sample can be determined. Such gas detection tubes are commercially available from, for example, Gastec Co. and Kitagawa Co.

According to the present invention, a method of measuring the level of an impurity in a gas stream is provided which employs a gas detection tube of the type normally used in air quality monitoring but which allows a large, measured quantity (typically 1 to 20 liters) of gas to pass through the detection tube, instead of the 100 to 400 ml employed in air quality monitoring. In this way, the level of the impurity in the gas stream can be determined in a simple and inexpensive manner well-suited to in situ application at a chemical process site while at the same time the minimum detection limit of the tube can be lowered significantly.

SUMMARY

In one aspect, the invention resides in a method of measuring the level of an impurity in a gas, the method comprising:
(a) providing a gas detection tube having an internal volume containing a reagent which can react with said impurity to produce a compound capable of producing a color change in said tube such that the extent of the color change is proportional to the concentration of the impurity in said gas;
(b) passing through said tube a volume of said gas at least $1 \times 10^3$ times the test volume of said tube; and
(c) measuring the extent of the color change of said detector element.

Conveniently, the volume of said gas at least $2 \times 10^3$ times, such as at least $5 \times 10^3$ times, for example at least $1 \times 10^4$ times, the internal volume of said tube.

Conveniently, the impurity is present in said gas at a concentration less than or equal to 5 ppm, such as less than or equal to 0.5 ppm, for example less than or equal to 0.05 ppm, such as less than or equal to 0.005 ppm, by weight of said gas.

Conveniently, the gas comprises a sample of a feed to a chemical process and the method further comprises adjusting the pressure of said gas to about 90 to 110 kPa prior to feeding said volume of gas to said tube. Generally, said adjusting comprises reducing the pressure of said gas.

Conveniently, the gas comprises at least one $C_1$ to $C_4$ hydrocarbon, particularly at least one $C_2$ to $C_4$ olefin.

In one embodiment, said gas comprises ethylene and said ethylene is a sample of an ethylene feed to a liquid phase, zeolite-catalyzed process for converting benzene to ethylbenzene.

In another embodiment, said gas comprises propylene and said propylene is a sample of a propylene feed to a liquid phase, zeolite-catalyzed process for converting benzene to cumene.

Conveniently, the impurity comprises at least one basic nitrogen compound, such as an alkyl amine and/or ammonia.

DETAILED DESCRIPTION OF THE EMBODIMENTS

Figure 1:
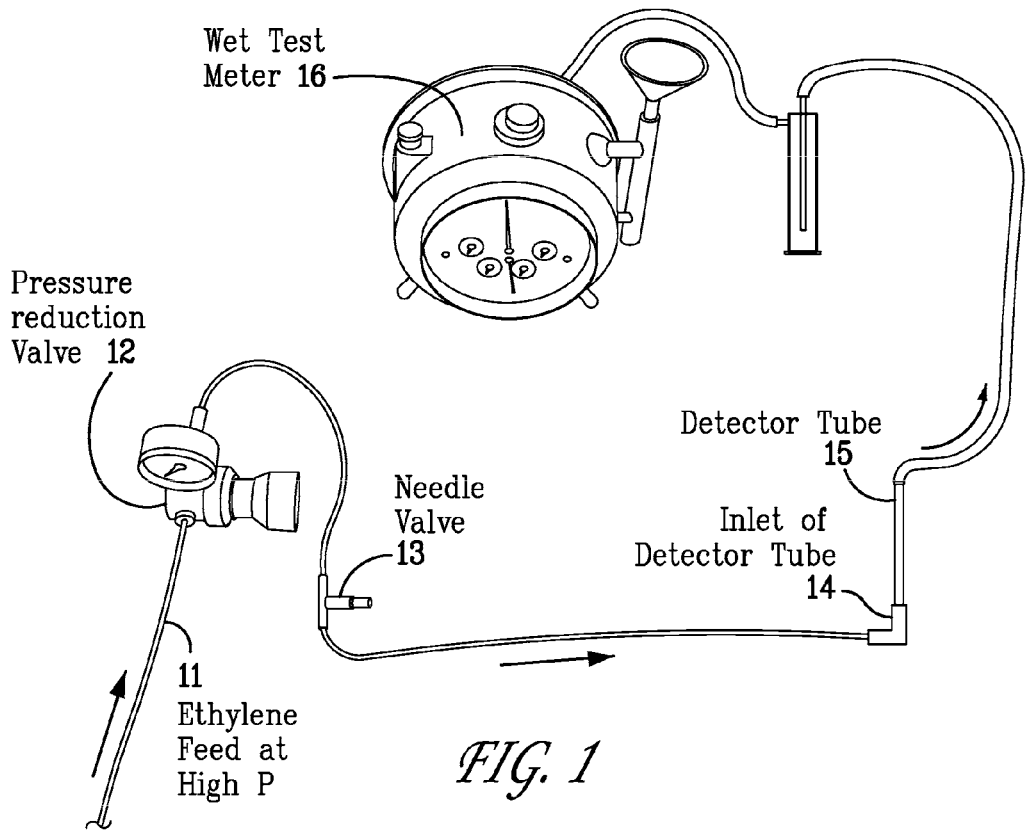
FIG. 1 is a schematic illustration of a method of measuring the level of impurity in ethylene in accordance with one example of the invention.

Described herein is a method of measuring the level of an impurity in a gas stream and, in particular, the level of a basic nitrogen impurity in a light hydrocarbon ($C_1$ to $C_4$) gas stream, such as a $C_2$ to $C_4$ olefin stream. The method has particular utility in measuring the level of basic nitrogen impurities in the olefin streams used in the zeolite-catalyzed, liquid phase alkylation of benzene with (a) ethylene to produce ethylbenzene and (b) propylene to produce cumene.

The method employs a gas detection tube, typically in the form of a sealed, hollow glass cylinder, which defines an internal test volume, typically of the order of 0.6 ml. Contained within the internal test volume of the tube is a reagent which can react with a specific impurity to be measured to produce a compound capable of generating a color change in a detector element in the detection tube such that the extent of the color change in the detector element is proportional to the concentration of the impurity. Generally, the extent of the color change is measured on a numerical scale printed directly on the tube.

Gas detection tubes of the type described above are conventionally employed in air quality monitoring and are commercially available from, for example, Gastec Co. and Kitagawa Co. Different tubes are employed to monitor different air components with, for example, the Gastec No. IG3HM tube being used to monitor ammonia levels and the Gastec No. IG180L tube being used to monitor dimethylamine levels. Other examples include Gastec No. IG19LA tube used for monitoring arsine levels, No. IG52 tube for monitoring acetonitrile levels, and No. IG191L tube for monitoring acrylonitrile levels. Another example is Kitagawa tube No. 8014-112SB used for monitoring hydrogen cyanide levels.

When used in air quality monitoring one of these tubes is unsealed (typically by breaking off the ends of the tube) and is inserted in the suction inlet of a hand-operated pump. The pump has a piston which, when retracted, draws through the tube a predetermined amount of air, V, generally of the order of 100 to 400 ml. Measuring the color change of the detector element gives a direct measurement of the amount of the designated component. When operated in this way, the detection tubes typically have a detection limit down to about 0.1 ppm of the designated impurity.

In the present method, instead of mounting the tube on a hand pump, the tube is connected to a supply of the gas to be monitored and a measured volume, Z, of the gas at least $1 \times 10^3$ times, typically at least $2 \times 10^3$ times, such as at least $5 \times 10^3$ times, even at least $1 \times 10^4$ times or even at least $2 \times 10^4$ times, the internal volume of the detection tube is passed through the tube and the extent of the color change of the detector element is measured. The amount of the impurity in the gas stream can then be determined by dividing the measured color change by Z/V. In this way, if, for example, Z/V is equal to 10, the detection limit of the tube for the specific impurity can be lowered by a factor of 10.

Generally, where the gas to be monitored is a feed to a chemical process, such as the liquid phase alkylation of benzene with a $C_2$ to $C_4$ olefin, the gas will be supplied at high pressure. In this case, the pressure of the gas is typically reduced to around atmospheric pressure, for example about 90 to 110 kPa, before the gas is supplied to the detection tube.

Referring now to the drawings, in the method shown in FIG. 1 a high pressure ethylene feed line 11 is connected by way of a pressure reduction valve 12 and a needle valve 13 to supply ethylene at atmospheric pressure to the inlet end 14 of a gas detection tube 15. At its outlet end, the tube 15 is connected to a metering device 16 for measuring the volume of ethylene that has flowed through the tube 15.

Figure 2:
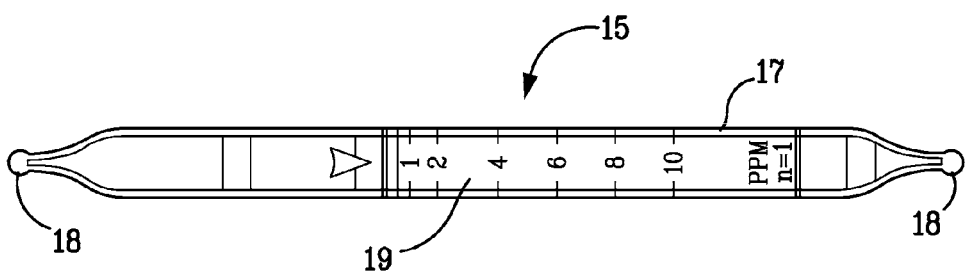
FIG. 2 is an enlarged view of a gas detector tube used in the method shown in FIG. 1.

The gas detection tube 15 is shown in more detail in FIG. 2 and includes a hollow cylindrical glass body 17 which, prior to use in the method of FIG. 1, is sealed at both ends by integral beads 18. Housed within the body 17 is a reagent (not shown) capable of reacting with a specific impurity, such as dimethylamine, in the ethylene feed to produce a compound capable of generating a color change visible on a scale 19 provided on the surface of the tube. Prior to connecting the tube 15 to the needle valve 13 and metering device 16, the beads 18 are broken to open the tube to the supply of ethylene to be monitored.

In some embodiments, this disclosure relates to:
Paragraph 1: A method of measuring the level of an impurity in a gas, the method comprising:

(a) providing a gas detection tube having an internal volume containing a reagent which can react with said impurity to produce a compound capable of producing a color change in said tube such that the extent of the color change is proportional to the concentration of the impurity in said gas;

(b) passing through said tube a volume of said gas at least $1 \times 10^3$ times the test volume of said tube; and (c) measuring the extent of the color change of said detector element.

Paragraph 2: The method of paragraph 1 wherein the volume of said gas at least $2 \times 10^3$ times, and preferably at least $5 \times 10^3$ times, more preferably at least $1 \times 10^4$ times, the internal volume of said tube.

Paragraph 3: The method of paragraph 1 or paragraph 2 wherein the impurity is present in said gas at a concentration less than or equal to 5 ppm, preferably less than or equal to 0.5 ppm, more preferably less than or equal to 0.05 ppm, most preferably less than or equal to 0.005 ppm, by weight of said gas.

Paragraph 4: The method of any preceding paragraph wherein the gas comprises a sample of a feed to a chemical process and the method further comprises adjusting the pressure of said gas to about 90 to 110 kPa prior to feeding said volume of gas to said tube.

Paragraph 5: The method of paragraph 4 wherein said adjusting comprises reducing the pressure of said gas.

Paragraph 6: The method of any preceding paragraph wherein the gas comprises at least one $C_1$ to $C_4$ hydrocarbon, preferably at least one $C_2$ to $C_4$ olefin.

Paragraph 7: The method of any preceding paragraph wherein the gas comprises ethylene.

Paragraph 8: The method of paragraph 7 wherein said ethylene is sample of an ethylene feed to a liquid phase, zeolite-catalyzed process for converting benzene to ethylbenzene.

Paragraph 9: The method of any one of paragraphs 1 to 6 wherein the gas comprises propylene.

Paragraph 10: The method of paragraph 9 wherein said propylene is sample of a propylene feed to a liquid phase, zeolite-catalyzed process for converting benzene to cumene.

Paragraph 11: The method of any preceding paragraph wherein the impurity comprises at least one basic nitrogen compound, preferably an alkylamine and/or ammonia.

Paragraph 12: The method of any one of paragraphs 1 to 10 wherein the impurity comprises at least one of hydrogen cyanide, a nitrile compound and arsine.

The invention will now be more particularly described with reference to the Example.

EXAMPLE

In an experiment, ethylene gas containing dimethylamine was passed at atmospheric pressure and a temperature of 20° C. through a Gastec No. IG180L detection tube having an internal volume of 0.6 ml and designed to operate with a test volume, V, of air of 100 ml. The gas was passed through the tube for a period of 2 hours, during which time volume of gas was measured as being 5.47 liters so that the flow rate was 2.74 liters/h. After 2 hours the gas flow was ceased and the color change in the tube from pink to orange was found to extend over 0.3 divisions of the scale on the tube. From this measurement, the dimethylamine concentration in the gas was calculated to be:

Dimethylamine=0.3×0.9×100/5470=0.005 ppm.

The manufacturer's suggested correction factor of 0.9 for dimethylamine is included in the above calculation.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method of measuring the level of an impurity in a gas, the method comprising:
    (a) providing a gas detection tube having an internal volume containing a reagent which can react with said impurity to produce a compound capable of producing a color change in a detector element in said tube such that the extent of the color change is proportional to the concentration of the impurity in said gas;
    (b) passing through said tube a volume of said gas at least $1 \times 10^3$ times the test volume of said tube; and
    (c) measuring the extent of the color change of said detector element, wherein the gas comprises a sample of a feed to a chemical process and the method further comprises adjusting the pressure of said gas to about 90 to 110 kPa prior to feeding said volume of said gas to said tube.

2. The method of claim 1 wherein the volume of said gas is at least $2 \times 10^3$ times the internal volume of said tube.

3. The method of claim 1 wherein the volume of said gas is at least $5 \times 10^3$ times the internal volume of said tube.

4. The method of claim 1 wherein the volume of said gas is at least $1 \times 10^4$ times the internal volume of said tube.

5. The method of claim 1 wherein the gas comprises at least one $C_1$ to $C_4$ hydrocarbon.

6. The method of claim 1 wherein the gas comprises at least one $C_2$ to $C_4$ olefin.

7. The method of claim 1 wherein the gas comprises ethylene.

8. The method of claim 7 wherein said ethylene is a sample of an ethylene feed to a liquid phase, zeolite-catalyzed process for converting benzene to ethylbenzene.

9. The method of claim 1 wherein the gas comprises propylene.

10. The method of claim 9 wherein said propylene is a sample of a propylene feed to a liquid phase, zeolite-catalyzed process for converting benzene to cumene.

11. The method of claim 1 wherein the impurity comprises at least one basic nitrogen compound.

12. The method of claim 1 wherein the impurity comprises an alkylamine and/or ammonia.

13. The method of claim 1 wherein the impurity comprises hydrogen cyanide or one or more nitrile compounds.

14. The method of claim 1 wherein the impurity comprises arsine.

15. The method of claim 1 further comprising the step:
    (d) determining the amount of the impurity in said volume of said gas.

16. The method of claim 15 wherein the impurity is present in said gas at a concentration less than or equal to 5 ppm by weight of said gas.

17. The method of claim 15 wherein the impurity is present in said gas at a concentration less than or equal to 0.5 ppm by weight of said gas.

18. The method of claim 15 wherein the impurity is present in said gas at a concentration less than or equal to 0.05 ppm by weight of said gas.

19. The method of claim 15 wherein the impurity is present in said gas at a concentration less than or equal to 0.005 ppm by weight of said gas.

* * * * *